United States Patent
Wu et al.

(10) Patent No.: US 6,904,118 B2
(45) Date of Patent: Jun. 7, 2005

(54) METHOD AND APPARATUS FOR GENERATING A DENSITY MAP USING DUAL-ENERGY CT

(75) Inventors: Xiaoye Wu, Rexford, NY (US); James LeBlanc, Niskayuna, NY (US); Armin Pfoh, Starnberg (DE)

(73) Assignee: General Electric Company, Schenectady, NY (US)

( * ) Notice: Subject to any disclaimer, the term of this patent is extended or adjusted under 35 U.S.C. 154(b) by 122 days.

(21) Appl. No.: 10/624,417

(22) Filed: Jul. 22, 2003

(65) Prior Publication Data

US 2004/0184574 A1 Sep. 23, 2004

Related U.S. Application Data

(60) Provisional application No. 60/397,658, filed on Jul. 23, 2002, and provisional application No. 60/398,463, filed on Jul. 25, 2002.

(51) Int. Cl.⁷ .............................................. G01N 23/00
(52) U.S. Cl. .............................. 378/5; 378/6; 378/207
(58) Field of Search ............................ 378/4, 5, 6, 18, 378/54, 56, 86, 207, 901

(56) References Cited

U.S. PATENT DOCUMENTS

| 5,335,260 A | 8/1994 | Arnold ........................ 378/207 |
| 5,867,553 A | 2/1999 | Gordon et al. .................. 378/4 |
| 6,233,304 B1 | 5/2001 | Hu et al. ....................... 378/8 |

FOREIGN PATENT DOCUMENTS

EP          03/22861          7/2003

*Primary Examiner*—David V. Bruce
*Assistant Examiner*—Courtney Thomas
(74) *Attorney, Agent, or Firm*—Fletcher Yoder (57) ABSTRACT

The present technique provides for the generation of density maps using one or more basis material decomposition tables or functions. The basis material decomposition tables or functions are generated by simulating the system response to various lengths of basis materials using component characteristics of the CT system as well as the attenuation coefficient for the desired basis material. Measured projection data may be processed using the basis material decomposition tables or functions to provide a set of density line-integral projections that may be reconstructed to form a density map or image.

54 Claims, 4 Drawing Sheets

METHOD AND APPARATUS FOR GENERATING A DENSITY MAP USING DUAL-ENERGY CT

CROSS-REFERENCE TO RELATED APPLICATIONS

This application claims the benefit of U.S. Provisional Application No. 60/397,658 filed on Jul. 23, 2002 and U.S. Provisional Application 60/398,463 filed on Jul. 25, 2002.

BACKGROUND OF THE INVENTION

The present invention relates generally to the field of medical imaging. In particular, the following techniques relate to dual energy computed tomography imaging systems and basis material decomposition within such systems.

Computed tomography (CT) imaging systems measure the intensity of X-ray beams passed through a patient from numerous angles. With sufficient angular coverage around the patient, cross-sectional images can be formed revealing the inner structure of the scanned object. The images are typically displayed on a cathode ray tube, and may be printed or reproduced on film. A virtual 3-D image may also be produced by a CT examination.

CT scanners operate by projecting X-ray beams from an X-ray source through an attenuating object, such as a patient. The X-ray beams may be collimated between the source and the object into a fan or cone shape, depending of the configuration of the detector, optimal patient exposure, or other factors. The attenuated beams are then detected by a set of detector elements. The detector element produces a signal based on the intensity of the X-ray beams. The measured data are then processed to represent the line integrals of the attenuation coefficients of the object along the ray paths. The processed data are typically called projections. By using reconstruction techniques, such as filtered backprojection, cross-sectional images are formulated from the projections. Adjacent cross-sectional images may be displayed together to render a volume representing the imaged region of the object or patient.

The X-ray beam attenuation caused by a given length of a material, such as bone or soft tissue, may be represented as an attenuation coefficient for that material. The attenuation coefficient of a material is a function of two separate events that may occur when an X-ray beam passes through a given length of the material. The first events, known as Compton scatter, denotes the tendency of an X-ray photon passing through the length of the material to be scattered or diverted from the original beam path, with a resultant change in energy. The second event, known as photoelectric absorption, denotes the tendency of an X-ray photon passing through the length of the material to be absorbed by the material.

As one might expect, different materials differ in their scatter and absorption properties, resulting in different attenuation coefficients for different materials. In particular, the probability of Compton scattering depends in part on the electron density of the imaged material and the probability of photoelectric absorption depends in part on the atomic number of the imaged material, i.e., the greater the atomic number, the greater the likelihood of absorption. Furthermore, both the Compton scattering effect and photoelectric absorption depend in part on the energy of the X-ray beam. As a result, materials can be distinguished from one another based upon the relative importance of the photoelectric absorption and Compton scattering effects in X-ray attenuation by the material.

In particular, measurement of the attenuation produced by a material at two X-ray energy levels or spectra, i.e., at dual energies, may allow for respective Compton scattering and photoelectric absorption contributions to be quantified for a material at the X-ray energy levels employed. In this manner, dual energy CT may provide spatial information in conjunction with information regarding the physical density and/or effective atomic number of the material or materials within the imaging volume. Using the spatial and density and/or atomic number information, an operator may reconstruct images that predominantly display selected materials, such as bone, soft tissue, or contrast agent, which differ in their atomic number or density. In this manner, a bone image, a soft tissue image, a contrast agent image, and so forth may be reconstructed which predominantly displays the material of interest. These images may in turn be associated to form a volume rendering of the material of interest which may be useful in determining bone density or deterioration, soft tissue damage, contrast agent perfusion, and so forth.

The process of decomposing the acquired data into the data associated with the basis materials, i.e., the materials for which images are desired, may be complex. In particular, the basis material decomposition (BMD) process typically involves a complicated mathematical inversion process. The inversion process may be inadequate to account for realistic system response, particularly for complex detector configurations or imperfect detector characteristics, and thus may be unable to accurately perform BMD in some circumstances. One solution to this imprecision has been to iteratively perform the inversion process until acceptable results are obtained. This solution, however, may be time-consuming and wasteful of computer resources. A rapid and accurate technique for performing BMD is therefore desirable.

BRIEF DESCRIPTION OF THE INVENTION

The present technique provides a novel approach for generating one or more density maps using a dual-energy CT system. For example, a basis material decomposition table or function may be generated by simulating the response of the CT system to various lengths of basis materials, taking into account the characteristics of the components of the system as well as the attenuation coefficient for the basis material. The characteristics of the components may include the X-ray spectra for a given peak kilovoltage and the detector response. The basis material decomposition table or function thus generated may be used to derive density line-integral projections determined from measured projection data. The density line-integral projections may in turn be reconstructed to generate a density map that is representative of the basis material. Series of density maps may be associated to form a volume rendering of the density or basis material in the imaged area.

In accordance with one aspect of the present technique, a method is provided for generating a basis material decomposition conversion table or function. One or more component characteristics of an X-ray imaging system are characterized and a pair of basis materials with respective attenuation coefficients are selected. A set of projection values for each of two or more energy spectra are generated, using the one or more component characteristics and the attenuation coefficients to simulate the responses of the X-ray imaging system to a plurality of lengths of the basis materials. At least one of a table and a function are generated from the sets of projection values and the one or more component characteristics. In addition, systems and computer programs in accordance with this aspect of the present technique are provided.

In accordance with another aspect of the present technique, a method is provided for generating a map of a basis material. A first projection set of an object at a first X-ray energy level and a second projection set of an object at a second X-ray energy level are generated. A line-integral projection set using the first projection set, the second projection set, and at least one basis material decomposition table or function is generated. The line-integral projection set is reconstructed to form a map. In addition, systems and computer programs in accordance with this aspect of the present technique are provided.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

Figure 1:
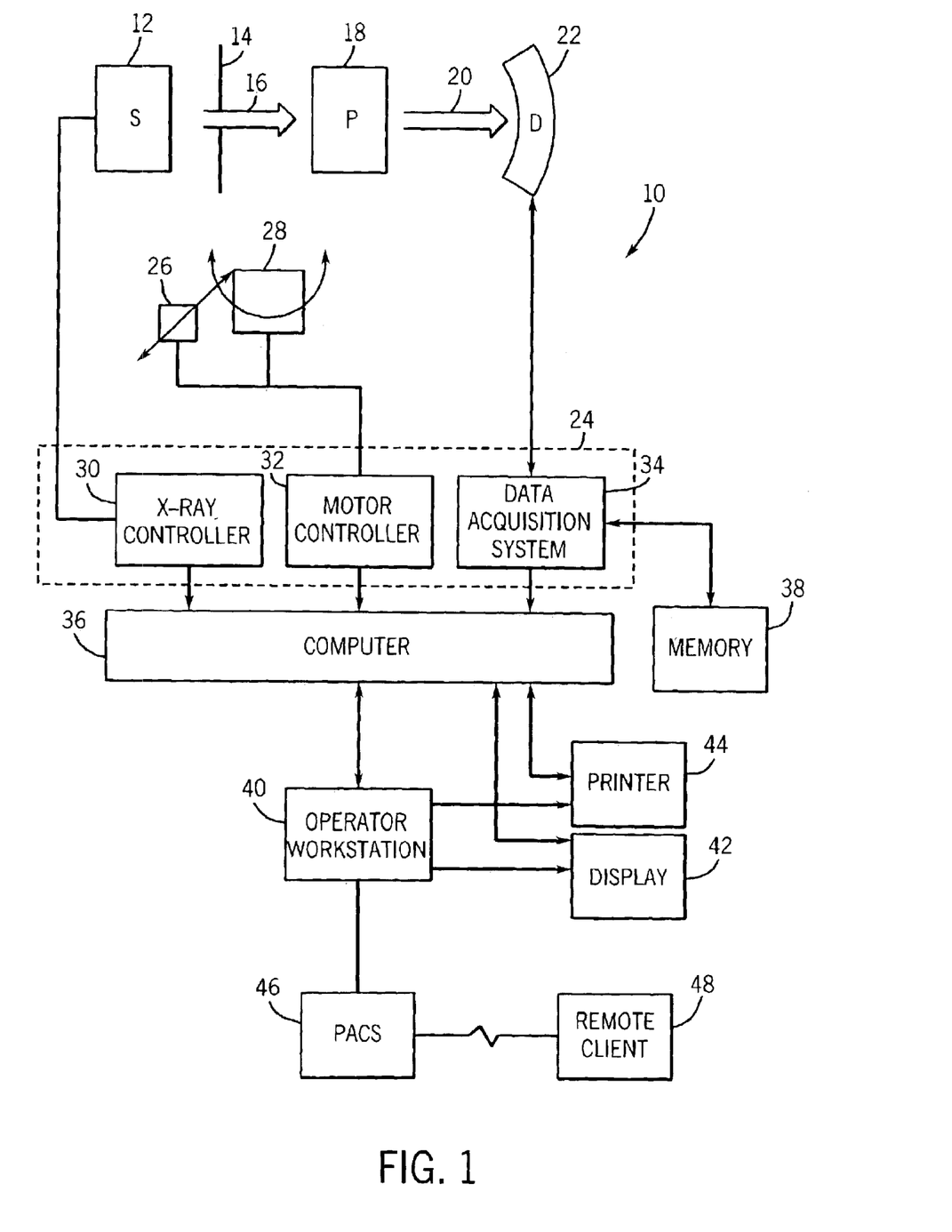
FIG. 1 is a diagrammatical view of an exemplary imaging system in the form of a CT imaging system for use in producing processed images in accordance with aspects of the present technique.

FIG. 1 illustrates diagrammatically an imaging system 10 for acquiring and processing image data. In the, illustrated embodiment, system 10 is a dual energy computed tomography (DE-CT) system designed to acquire image data at two or more X-ray energy levels or spectra and to process the image data for display and analysis in accordance with the present technique. Though the present discussion will be presented in the context of a DE-CT system, such as the one depicted, it should be understood that the present technique is equally applicable to dual-energy X-ray imaging in other contexts such as projection X-ray imaging or tomosynthesis. Alternately, the imaging system 10 may be designed to acquire image data at a single spectrum using a detector with energy resolution, which allows the energy level of each detected photon to be assessed. In the embodiment illustrated in FIG. 1, imaging system 10 includes a source of X-ray radiation 12 positioned adjacent to a collimator 14. In this exemplary embodiment, the source of X-ray radiation source 12 is typically an X-ray tube.

Collimator 14 permits a stream of radiation 16 to pass into a region in which a subject, such as a human patient 18 is positioned. A portion of the radiation 20 passes through or around the subject and impacts a detector array, represented generally at reference numeral 22. Detector elements of the array produce electrical signals that represent the intensity of the incident X-ray beam. These signals are acquired and processed to reconstruct an image of the features within the subject. As noted above, the DE-CT system may incorporate a source of X-ray radiation 12 which may be adjusted or configured to emit X-ray at more than one energy level or spectrum or a detector 22 with energy resolution capabilities.

A system controller 24 may control the source 12. The system controller 24 typically furnishes both power, and control signals for CT examination sequences. Moreover, the detector 22 is coupled to the system controller 24, which controls the acquisition of the signals generated in the detector 22. The system controller 24 may also execute various signal processing and filtration functions, such as for initial adjustment of dynamic ranges, interleaving of digital image data, and so forth. In general, system controller 24 commands operation of the imaging system to execute examination protocols and to process acquired data. In the present context, system controller 24 also includes signal processing circuitry, typically based upon a general purpose or application-specific digital computer, associated memory circuitry for storing programs and routines executed by the computer, as well as configuration parameters and image data, interface circuits, and so forth.

In the embodiment illustrated in FIG. 1, system controller 24 is coupled to a linear positioning subsystem 26 and rotational subsystem 28. The rotational subsystem 28 enables the X-ray source 12, collimator 14 and the detector 22 to be rotated one or multiple turns around the patient 18. It should be noted that the rotational subsystem 28 might include a gantry. Thus, the system controller 24 may be utilized to operate the gantry. The linear positioning subsystem 26 enables the patient 18, or more specifically a patient table, to be displaced linearly. Thus, the patient table may be linearly moved within the gantry to generate images of particular areas of the patient 18.

Additionally, as will be appreciated by those skilled in the art, the source of radiation may be controlled by an X-ray controller 30 disposed within the system controller 24. Particularly, the X-ray controller 30 is configured to provide power and timing signals to the X-ray source 12 and may determine what X-ray energy level or spectrum the source 12 emits. A motor controller 32 may be utilized to control the movement of the rotational subsystem 28 and the linear positioning subsystem 26.

Further, the system controller 24 is also illustrated comprising a data acquisition system 34. In this exemplary embodiment, the detector 22 is coupled to the system controller 24, and more particularly to the data acquisition system 34. The data acquisition system 34 receives data collected by readout electronics of the detector 22. The data acquisition system 34 typically receives sampled analog signals from the detector 22 and converts the data to digital signals for subsequent processing by a computer 36.

The computer 36 is typically coupled to the system controller 24. The data collected by the data acquisition system 34 may be transmitted to the computer 36 for subsequent processing and reconstruction. The computer 36 may comprise or communicate with a memory 38 that can store data processed by the computer 36 or data to be processed by the computer 36. It should be understood that any type of computer accessible memory device capable of storing the desired amount of data and/or code may be utilized by such an exemplary system 10. Moreover, the memory 38 may comprise one or more memory devices, such as magnetic or optical devices, of similar or different types, which may be local and/or remote to the system 10. The memory 38 may store data, processing parameters, and/or computer programs comprising one or more routines for performing the processes described herein.

The computer 36 may also be adapted to control features enabled by the system controller 24, i.e., scanning operations and data acquisition. Furthermore, the computer 36 may be configured to receive commands and scanning parameters from an operator via an operator workstation 40 typically equipped with a keyboard and other input devices (not shown). An operator may thereby control the system 10 via the input devices. Thus, the operator may observe the reconstructed image and other data relevant to the system from computer 36, initiate imaging, and so forth.

An operator may control the system 10 via the input devices. Thus, the operator may observe the reconstructed image and other data relevant to the system from computer 36, initiate imaging, and so forth. Similarly, a display 42 coupled to the operator workstation 40 may allow an operator to observe the reconstructed image and to control imaging. Additionally, a reconstructed image may also be printed by a printer 44 which may be coupled to the operator workstation 40. The display 42 and printer 44 may also be connected to the computer 36, either directly or via the operator workstation 40. Further, the operator workstation 40 may also be coupled to a picture archiving and communications system (PACS) 46. It should be noted that PACS 46 might be coupled to a remote system 48, radiology department information system (RIS), hospital information system (HIS) or to an internal or external network, so that others at different locations may gain access to the image and to the image data.

It should be further noted that the computer 36 and operator workstation 40 may be coupled to other output devices, which may include standard, or special purpose computer monitors and associated processing circuitry. One or more operator workstations 40 may be further linked in the system for outputting system parameters, requesting examinations, viewing images, and so forth. In general, displays, printers, workstations, and similar devices supplied within the system may be local to the data acquisition components, or may be remote from these components, such as elsewhere within an institution or hospital, or in an entirely different location, linked to the image acquisition system via one or more configurable networks, such as the Internet, virtual private networks, and so forth.

Figure 2:
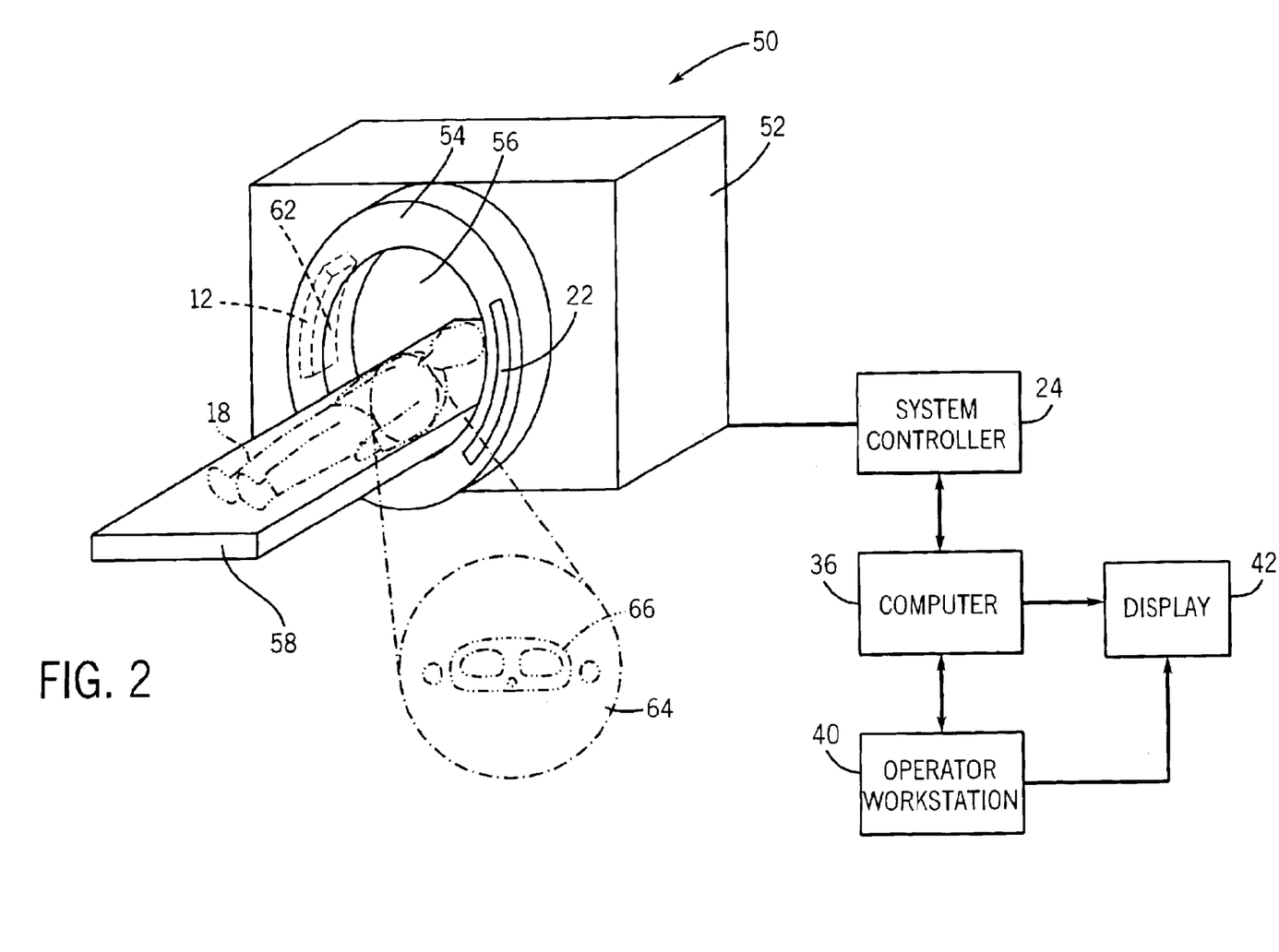
FIG. 2 is another diagrammatical view of a physical implementation of the CT system of FIG. 1.

Referring generally to FIG. 2, an exemplary imaging system utilized in a present embodiment may be a DE-CT scanning system 50. The DE-CT scanning system 50 may be a multi-slice detector system that offers a wide array of axial coverage, high gantry rotational speed, and high spatial resolution. The DE-CT scanning system 50 is illustrated with a frame 52 and a gantry 54 that has an aperture 56. Further, a patient table 58 is illustrated positioned in the aperture 56 of the frame 52 and the gantry 54. The patient table 58 is adapted so that a patient 18 may recline comfortably during the examination process. Additionally, the patient table 58 is configured to be displaced linearly by the linear positioning subsystem 26 (see FIG. 1). The gantry 54 is illustrated with the source of radiation 12, typically an X-ray tube that emits X-ray radiation from a focal point 62.

In typical operation, X-ray source 12 projects an X-ray beam of a selected energy level or spectrum from the focal point 62 and toward detector array 22. The detector 22 is generally formed by a plurality of detector elements, which sense the X-rays that pass through and around a subject of interest, such as the heart and chest. Each detector element produces an electrical signal that represents the intensity of the X-ray beam at the position of the element at the time the beam strikes the detector. The gantry 54 is rotated around the subject of interest so that a plurality of radiographic views may be collected by the computer 36.

An image or slice is computed which may incorporate, in certain modes, less or more than 360 degrees of projection data, to formulate an image. The image may be collimated to desired dimensions, using tungsten shutters in front of the X-ray source 12 and different detector apertures. The collimator 14 (see FIG. 1) typically defines the size and shape of the X-ray beam that emerges from the X-ray source 12. In addition, a bowtie filter may be included in the system 50 to further control the patient dose. In particular, the bowtie filter pre-attenuates the X-rays to accommodate the body part being imaged, such as head or torso, such that, in general, less attenuation is provided for X-rays passing through or near the isocenter 72. In this manner, the bowtie filter conforms the X-ray intensity during imaging in accordance with the region being imaged.

Thus, as the X-ray source 12 and the detector 22 rotate, the detector 22 collects data of the attenuated X-ray beams. The data collected by the detector 22 undergoes pre-processing and calibration to condition the data to represent the line integrals of the attenuation coefficients of the scanned object. The processed data are commonly called projections.

In DE-CT, two (or more) sets of projection data are obtained for the imaged object at different tube voltages or different X-ray spectra or, alternately, at a single tube voltage or spectrum with an energy resolving detector 22. The acquired sets of projection data may be used for basis material decomposition (BMD). During BMD, the measured projections are converted to a set of density line-integral projections. The density line-integral projections may be reconstructed to form a density map or image of each respective basis material, such as bone, soft tissue, and/or contrast agent maps. The density maps or images may be, in turn, associated to form a volume rendering of the basis material, i.e., bone, soft tissue, and/or contrast agent, in the imaged volume.

Once reconstructed, the basis material image 64 produced by the system of FIGS. 1 and 2 reveals internal features of a patient, expressed in the densities of the two-basis materials. As illustrated generally in FIG. 2, the density image 64 may be displayed to show these features, such as indicated at reference numeral 66 in FIG. 2. In traditional approaches to diagnosis of medical conditions, such as disease states, and more generally of medical events, a radiologist or physician would consider a hard copy or display of the density image 64 to discern characteristic features of interest. Such features might include lesions, sizes and shapes of particular anatomies or organs, and other features that would be discernable in the image based upon the skill and knowledge of the individual practitioner.

As noted in the above discussion, the processing of the measured projection data to generate a density image typically involves a BMD process. The BMD process may be performed via a mathematical inversion process. The inversion process, however, typically fails to incorporate realistic system responses. As a result, BMD processes accomplished via mathematical inversion may be inaccurate or unreliable for various system configurations, such as for complex detector configurations. To address these deficiencies, the inversion process may be iteratively performed until acceptable results are obtained.

Alternatively, the BMD process may be accomplished using a BMD conversion table or function that accounts for the system characteristics. The BMD conversion table or function may, thereby, accurately represent realistic system response. Furthermore, because the BMD conversion table or function may be pre-generated, BMD may be accomplished rapidly, without iterative processing to arrive at an acceptable solution set.

Figure 3:
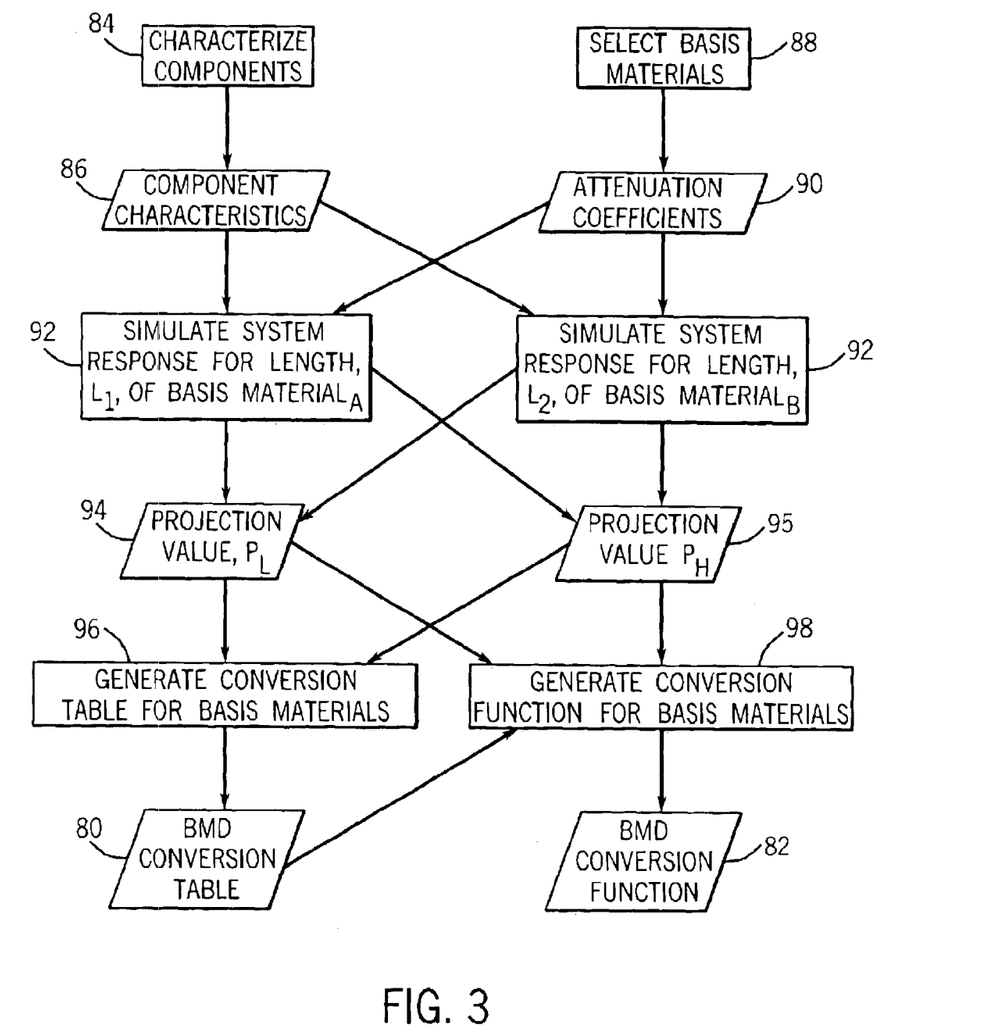
FIG. 3 is a flowchart depicting steps for generating a basis material decomposition table or function in accordance with one aspect of the present technique.

For example, referring to FIG. 3, a technique for generating a BMD conversion table 80 or function 82 is depicted. One or more components of the X-ray imaging system, such as DE-CT system 50, are characterized, as depicted at step 84. The components to be characterized may include, but are not limited to, the detector, source, filter, data acquisition system 34, and so forth. Examples of component characteristics 86 include, but are not limited to, the X-ray spectrum, the beam filter, the detector response, the X-ray energy level, and the peak kilovoltage (kVp). The component characteristics 86 relate to the configuration of the DE-CT system 50 and provide information that may be used to determine realistic system responses.

A basis material system consisting of two distinctive materials, such as bone, soft tissue, or contrast agent, or a pair of other materials, is selected for simulation at step 88. The respective attenuation coefficients 90 associated with the basis materials may be used, in conjunction with the component characteristics 86 to simulate the system response for varying lengths, L, of the basis materials, as depicted at step 92.

As depicted at step 92, $L_1$ and $L_2$ represent the varying lengths of the different basis respectively. The simulation process may be based upon known mathematical principles in which the respective component characteristics 86 and attenuation coefficients 90 are modeled to generate respective projection values, P, 94 for each length, L. Various lengths may be simulated at step 92 such that the entire dynamic range of the system 50 is covered, though less than the dynamic range may also be simulated. Through the system simulation process, input data pairs ($L_1$, $L_2$) and the simulated low and high energies spectra generate respective output projection values ($P_L$, $P_H$), where $P_L$ 94 are the projection values generated at the low energy spectrum and $P_H$ 95 are the projection values generated at the high energy spectrum.

Once the sets of projection values 94, 95 are obtained for the respective lengths of the basis materials covering the desired dynamic range, a BMD conversion table 80 may be generated, as depicted at step 96. The BMD conversion table 80 may relate a projection value 94 to a length of a basis material based upon the various component characteristics 86 and the attenuation coefficient 90 of the basis material. In particular, by inverting the input and output, one can generate BMD conversion table 80. The data pair ($L_1$, $L_2$) is the integrated lengths for the basis material, which can be directly associated with the integrated densities for the basis material if one prefers to obtain the density map for the reconstructed images. To facilitate the conversion process, the BMD conversion table 80 may include interpolated projection values 94 that are evenly and incrementally spaced in the table 80.

A BMD conversion function 82 may be generated in addition to or in place of the conversion table 80, as depicted by step 98. For example, the conversion table 80 may be surface fitted with a high-order polynomial to generate the conversion function 82. Alternately, a high-order polynomial may be fitted directly to the projection values 94, component characteristics 86, and attenuation coefficient 90 to generate the BMD conversion function 82. In some circumstances, such as when a bowtie is present in the DE-CT system 50, a separate conversion table 80 or function 82 may be generated for each detector channel of the detector array 22.

Therefore, using the BMD conversion table 80, a density line-integral projection set for the basis material may be determined from a measured projection set and the component characteristics 86 of the system 50 at the time of measurement. For example, referring to FIG. 4, the use of a BMD conversion table 80, or alternately a BMD conversion function 82, is described in greater detail. An object or patient is typically imaged at a first and second X-ray energy level, as depicted at steps 110 and 112 respectively, to produce first and second sets of projection data, 114 and 116 respectively. The first and second X-ray energy levels typically correspond to distinct X-ray spectra that are differentially attenuated by the basis materials of interest. Alternately, the object or patient may be imaged at a single X-ray spectrum using an energy resolving detector capable of associating a measured energy level with each detected photon. While measurements are depicted as being made using two X-ray energy levels, measurements may be made using additional X-ray energy levels if desired, for example, when x-ray scatter becomes significant.

Figure 4:
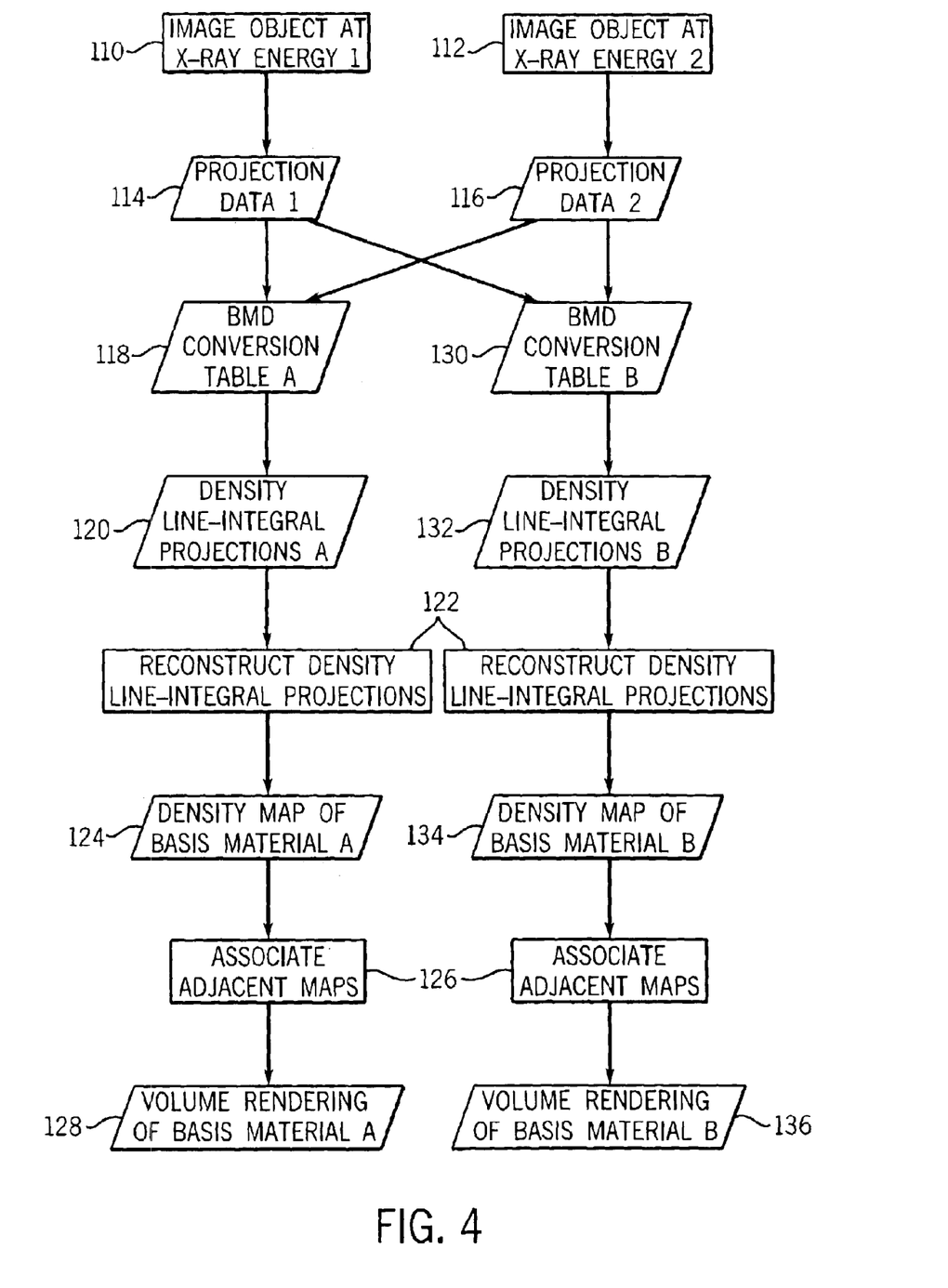
FIG. 4 is a flowchart depicting steps for generating a density map in accordance with one aspect of the present technique.

The projection values of the first and second projection data sets 114, 116 may be searched for in the BMD conversion table 118 associated with basis material A and the corresponding density line integral projections 120 retrieved from the table 118. As depicted at step 122, the retrieved density line integral projections 120 may then be reconstructed with a conventional technique, such as by filtered backprojection, to generate a density map 124 or image of basis material A. The density map corresponds to the presence of the basis material, such as bone, soft tissue, or contrast agent, at the axial position represented by the projections. Density maps 124 for proximate or adjacent axial positions, or z-locations, may be associated, as depicted at step 126, to generate a volume rendering 128 of basis material A for the imaged volume. While the described conversion table 118 represents one mechanism of generating density line integrals 120 from the projection data 114, 116, one of ordinary skill in the art will readily understand that a conversion function 82, as described above, may also be used.

Similarly, the projection values of the first and second projection data sets 114, 116 may be searched for in the BMD conversion table 130 associated with basis material B and the corresponding density line integral projections 132 retrieved from the table 130. A corresponding density map 134 of basis material B may be reconstructed and, if desired, proximate or adjacent density maps 122 may be associated to form a volume rendering 136 of basis material B for the imaged volume.

In addition, using the combined information from the basis material conversion tables 118, 130 the projection data from the projection data sets 114, 116 may be processed to generate density line integral projections for basis materials other than those associated with the tables 120, 132, i.e., for basis materials C, D, and so forth. In particular, because the density of other basis materials may be represented as a combination of the density information associated with the basis materials A and B, the information contained with the conversion tables 118, 130 may be combined to generate the density line integral projections associated with other basis materials. Furthermore, the BMD decomposition technique described herein can be to decompose the photoelectric and Compton components for an imaged material. Therefore, if desired, images corresponding to the photoelectric or Compton components of the imaged material may be generated in addition to or instead of the density based images.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A method for generating a basis material decomposition conversion table or function, comprising:

characterizing one or more component characteristics of an X-ray imaging system;

selecting a pair of basis materials with respective attenuation coefficients;

generating a set of projection values for each of two or more energy spectra using the one or more component characteristics and the attenuation coefficients to simulate the responses of the X-ray imaging system to a plurality of lengths of the basis materials; and generating at least one of a table and a function from the sets of projection values and the one or more component characteristics.

2. The method as recited in claim 1, wherein the one or more components comprise at least one of a detector array, an X-ray source, and an X-ray filter.

3. The method as recited in claim 2, wherein characterizing at least one of the X-ray source and the X-ray filter comprises characterizing at least one of a peak kilovoltage, an X-ray energy level, and an X-ray spectrum.

4. The method as recited in claim 2, wherein characterizing the detector array comprises characterizing a detector response.

5. The method as recited in claim 1, wherein the X-ray imaging system comprises a dual-energy CT imaging system.

6. The method as recited in claim 1, wherein the X-ray imaging system comprises a dual-energy projection X-ray imaging system or a dual-energy X-ray tomosynthesis imaging system.

7. The method as recited in claim 1, wherein the basis materials comprise at least one of bone, soft tissue, and contrast agent.

8. The method as recited in claim 1, wherein the plurality of lengths of the basis materials represent the dynamic range of the X-ray imaging system.

9. The method as recited in claim 1, wherein the sets of projection values comprise one or more interpolated projection values.

10. The method as recited in claim 1, further comprising determining a density line integral set for one of the basis materials using a measured projection set and at least one of the table and the function.

11. The method as recited in claim 1, further comprising determining a line integral set representative of a photoelectric effect or a Compton effect for one of the basis materials using a measured projection set and at least one of the table and the function.

12. A method for generating a map of a basis material, comprising:

generating a first projection set of an object at a first X-ray energy level and a second projection set of an object at a second X-ray energy level;

generating a line-integral projection set using the first projection set, the second, projection set, and at least one basis material decomposition table or function; and reconstructing the line-integral projection set to form a map.

13. The method as recited in claim 12, wherein the line-integral projection set comprises one of a density line-integral projection set, a photoelectric line integral projection set, and a Compton line integral projection set.

14. The method as recited in claim 12, wherein the line-integral projection set comprises a density line integral projection set and the map comprises a density map.

15. The method as recited in claim 12, wherein the at least one basis material decomposition table or function is a basis material decomposition table or function associated with a basis material and the density map comprises a map of the basis material.

16. The method as recited in claim 15, wherein the basis material comprises one of bone, soft tissue, and contrast agent.

17. The method as recited in claim 12, wherein the at least one basis material decomposition table or function comprises at least one of a bone decomposition table or function, a soft tissue decomposition table or function, and a contrast agent decomposition table or function.

18. The method as recited in claim 12, wherein the at least one basis material decomposition table or function comprises a bone decomposition table or function and the density map comprises a bone map.

19. The method as recited in claim 12, wherein the at least one basis material decomposition table or function comprises a soft tissue decomposition table or function and the density map comprises a soft tissue map.

20. The method as recited in claim 12, wherein the at least one basis material decomposition table or function comprises a contrast agent decomposition table or function and the density map comprises a contrast agent map.

21. The method as recited in claim 12, further comprising associating the density map with one or more adjacent density maps to form a volume rendering.

22. A computer program, provided on one or more computer readable media, for generating a basis material decomposition conversion table or function, comprising:

a routine for generating a set of projection values for each of two or more energy spectra using one or more component characteristics of an X-ray imaging system and attenuation coefficients for a pair of basis materials to simulate the responses of the X-ray imaging system to a plurality of lengths of the basis materials; and a routine for generating at least one of a table and a function from the sets of projection values and the one or more component characteristics.

23. The computer program as recited in claim 22, wherein the one or more component characteristics comprise a peak kilovoltage, an X-ray energy level, an X-ray spectrum, a detector response.

24. The computer program as recited in claim 22, wherein the X-ray imaging system comprises one of a dual-energy CT imaging system, a dual-energy projection X-ray imaging system, and a dual-energy X-ray tomosynthesis imaging system.

25. The computer program as recited in claim 22, wherein the basis materials comprise at least one of bone, soft tissue, and contrast agent.

26. The computer program as recited in claim 22, further comprising a routine for calculating one or more interpolated projection values for inclusion in one or the sets of projection values.

27. The computer program as recited in claim 22, further comprising a routine for determining a density line integral set for one of the basis materials using a measured projection set and at least one of the table and the function.

28. The computer program as recited in claim 22, further comprising a routine for determining a line integral set representative of a photoelectric effect or a Compton effect for one of the basis materials using a measured projection set and at least one of the table and the function.

29. A computer program, provided on one or more computer readable media, for generating a map of a basis material, comprising:
a routine for generating a first projection set of an object at a first X-ray energy level and a second projection set of an object at a second X-ray energy level;
a routine for generating a line-integral projection set using the first projection set, the second projection set, and at least one basis material decomposition table or function; and
a routine for reconstructing the line-integral projection set to form a map.

30. The computer program as recited in claim 29, wherein the line-integral projection set comprises one of a density line-integral projection set, a photoelectric line integral projection set, and a Compton line integral projection set.

31. The computer program as recited in claim 29, wherein the line-integral projection set comprises a density line integral projection set and the map comprises a density map.

32. The computer programs as recited in claim 29, wherein the at least one basis material decomposition table or function is a basis material decomposition table or function associated with a basis material and the density map comprises a map of the basis material.

33. The computer program as recited in claim 32, wherein the basis material comprises one of bone, soft tissue, and contrast agent.

34. The computer program as recited in claim 29, wherein the at least one basis material decomposition table or function comprises at least one of a bone decomposition table or function, a soft tissue decomposition table or function, and a contrast agent decomposition table or function.

35. The computer program as recited in claim 29, wherein the at least one basis material decomposition table or function comprises a bone decomposition table or function and the density map comprises a bone map.

36. The computer program as recited in claim 29, wherein the at least one basis material decomposition table or function comprises a soft tissue decomposition table or function and the density map comprises a soft tissue map.

37. The computer program as recited in claim 29, wherein the at least one basis material decomposition table or function comprises a contrast agent decomposition table or function and the density map comprises a contrast agent map.

38. The computer program as recited in claim 29, further comprising a routine for associating the density map with one or more adjacent density maps to form a volume rendering.

39. A X-ray image analysis system comprising:
an X-ray source configured to emit a stream of radiation;
an X-ray filter configured to filter the stream of radiation;
a detector configured to detect the stream of radiation and to generate one or more signals responsive to the stream of radiation, wherein the detector comprises a plurality of detector elements;
a system controller configured to control the X-ray source and to acquire a set of projection data from one or more of the detector elements via a data acquisition system; and
a computer system configured to generate a set of projection values for each of two or more energy spectra using attenuation coefficients for a pair of basis materials and one or more component characteristics of at least one of the X-ray source, the X-ray filter and the detector to simulate the responses of the detector to a plurality of lengths of the basis materials, and to generate at least one of a table and a function from the sets of projection values and the one or more component characteristics.

40. The X-ray image analysis system as recited in claim 39, wherein the one or more component characteristics comprise at least one of a peak kilovoltage, an X-ray energy level, an X-ray spectrum, and a detector response.

41. The X-ray image analysis system as recited in claim 39, wherein the basis materials comprise at least one of bone, soft tissue, and contrast agent.

42. The X-ray image analysis system as recited in claim 39, wherein the computer is further configured to determine a density line integral set for one of the basis materials using the set of projection data and at least one of the table and the function.

43. The X-ray image analysis system as recited in claim 39, wherein the computer is further configured to determine a line integral set representative of a photoelectric effect or a Compton effect for one of the basis materials using the set of projection data and at least one of the table and the function.

44. An X-ray image analysis system, comprising:
an X-ray source configured to emit a stream of radiation;
a detector configured to detect the stream of radiation and to generate one or more signals responsive to the stream of radiation, wherein the detector comprises a plurality of detector elements;
a system controller configured to control the X-ray source and to acquire a first projection set of an object at a first X-ray energy level and a second projection set of an object at a second X-ray energy level from one or more of the detector elements via a data acquisition system; and
a computer system configured to generate a line-integral projection set using the first projection set, the second projection set, and at least one basis material decomposition table or function and to reconstruct the line-integral projection set to form a map.

45. The X-ray image analysis system as recited in claim 44, wherein the line-integral projection set comprises one of a density line-integral projection set, a photoelectric line integral projection set, and a Compton line integral projection set.

46. The X-ray image analysis system as recited in claim 44, wherein the line-integral projection set comprises a density line integral projection set and the map comprises a density map.

47. The X-ray image analysis system as recited in claim 44, wherein the at least one basis material decomposition table or function is a basis material decomposition table or function associated with a basis material and the density map comprises a map of the basis material.

48. The X-ray image analysis system as recited in claim 47, wherein the basis material comprises one of bone, soft tissue, and contrast agent.

49. The X-ray image analysis system as recited in claim 44, wherein the computer is further configured to associate the density map with one or more adjacent density maps to form a volume rendering.

50. A X-ray image analysis system, comprising:
an X-ray source configured to emit a stream of radiation;

an X-ray filter configured to filter the stream of radiation;

a detector configured to detect the stream of radiation and to generate one or more signals responsive to the stream of radiation, wherein the detector comprises a plurality of detector elements;

a system controller configured to control the X-ray source and to acquire a set of projection data from one or more of the detector elements via a data acquisition system;

a computer system configured to receive the set of projection data;

means for simulating the responses of the detector to a plurality of lengths of a pair of basis materials at two or more energy spectra to generate a set of projection values for each of two or more energy spectra; and means for generating a basis material decomposition table or function from the sets of projection values.

51. The X-ray image analysis system as recited in claim 50, wherein the means for simulating utilizes at least one of peak kilovoltage, an X-ray energy level, an X-ray spectrum, and a detector response.

52. The X-ray image analysis system as recited in claim 50, wherein the basis materials comprise at least one of bone, soft tissue, and contrast agent.

53. The X-ray image analysis system as recited in claim 50, further comprising means for determining a density line integral set for one of the basis materials using the set of projection data and at least one of the table and the function.

54. The X-ray image analysis system as recited in claim 50, further comprising means for determining a line integral set representative of a photoelectric effect or a Compton effect for one of the basis materials using the set of projection data and at least one of the table and the function.

* * * * *